(12) United States Patent
Saltiel

(10) Patent No.: US 7,211,172 B1
(45) Date of Patent: May 1, 2007

(54) METHOD OF PHOTOCHEMICAL SYNTHESIS OF VITAMIN DS

(75) Inventor: Jack Saltiel, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 306 days.

(21) Appl. No.: 10/649,287

(22) Filed: Aug. 27, 2003

Related U.S. Application Data

(60) Provisional application No. 60/407,137, filed on Aug. 29, 2002.

(51) Int. Cl.
*C07C 401/00* (2006.01)

(52) U.S. Cl. .................................. 204/157.67

(58) Field of Classification Search ............ 204/157.67
See application file for complete search history.

(56) References Cited

U.S. PATENT DOCUMENTS 4,388,242 A * 6/1983 Malatesta et al. ............ 552/653
4,686,023 A * 8/1987 Stevens .................. 204/157.67
6,902,654 B2 * 6/2005 Michishita et al. ..... 204/157.67

* cited by examiner

*Primary Examiner*—Edna Wong
(74) *Attorney, Agent, or Firm*—Allen, Dyer, Doppelt, Milbrath & Gilchrist, P.A.

(57) ABSTRACT

An enhanced photochemical method of making vitamin D includes irradiating a reaction mixture of precursor molecules with light having a wavelength of 254 nm and with light having a wavelength of 313 nm to produce previtamin D, and is followed by heating at a temperature not exceeding 100° C. to convert previtamin D to vitamin D.

16 Claims, 17 Drawing Sheets

METHOD OF PHOTOCHEMICAL SYNTHESIS OF VITAMIN DS

RELATED APPLICATION

This application claims benefit from co-pending provisional application Ser. No. 60/407,137, which was filed on Aug. 29, 2002, and which is incorporated herein by reference in its entirety.

FIELD OF THE INVENTION

The present invention relates to the field of molecular synthesis and, more particularly, to the photochemical synthesis of vitamin D from precursor molecules.

REFERENCES CITED

1. For reviews see (a) Jacobs, H. J. C. and Havinga, E. Photochemistry of vitamin D and its isomers and of simple trienes, *Adv. Photochem.*, 11, 305–373, 1979. (b) Jacobs, H. J. C. and Laarhoven, W. H., Photochemistry of vitamin D and related compounds, In *Handbook of Organic Photochemistry and Photobiology*, Horspool, W. M. and Song, P.-O., Eds.; CRC Press: London, 1995, Section 1, 155–164.
2. For reviews see (a) Dauben, W. G., Kellogg, M. S., Seeman, J. I., Vietmeyer, N. D. and Wendschuh, P. H., Steric aspects of the photochemistry of conjugated dienes and trienes, *Pure Appl. Chem.*, 33, 197–215, 1973. (b) Dauben, W. G., McInnis, E. L. and Michno, D. M., Photochemical rearrangements in trienes, In *Rearrangements in Ground and Excited States*, (P. de Mayo, Ed.), 1980, Vol III, 91–129.
3. (a) Havinga, E. and Schlatmann, J. L. M. A., Remarks on the specificities of the photochemical and thermal transformations in the vitamin D field, *Tetrahedron*, 16, 146–152, 1961. (b) Havinga, E., Über einige photochemische Reactionen, *Chimia*, 16, 145, 1962.
4. (a) Hammond, G. S. and Liu, R. S. H., Stereoisomeric triplet states of conjugated dienes, *J. Am. Chem. Soc.*, 85, 477–478, 1963. (b) Liu, R. S. H., Turro, N. J. and Hammond, G. S., Activation and deactivation of conjugated dienes by energy transfer, *J. Am. Chem. Soc.*, 87, 3406–3412, 1965.
5. Hammond, G. S., Saltiel, J., Lamola, A. A., Turro, N. J., Bradshaw, J. S., Cowan, D. O., Counsell, R. C., Vogt, V. and Dalton, C., Photochemical cis-trans isomerization, *J. Am. Chem. Soc.*, 86, 3197–3217, 1964.
6. Saltiel, J., Metts, L., Sykes, A. and Wrighton, M., The role of s-cis-1,3-diene triplets in sensitized cis-trans photoisomerization, *J. Am. Chem. Soc.*, 93, 5302–5303, 1971.
7. Baldwin, J. E. and Krueger, S. M., Stereoselective photochemical electrocyclic valence isomerizations of α-phellandrene conformational isomers, *J. Am. Chem. Soc.*, 91, 6444–6447, 1969.
8. Saltiel, J., Sears, Jr., D. F., Sun, Y.-P. and Choi, J.-O., Evidence for ground state s-cis-conformers in the fluorescence spectra of all-trans-1,6-diphenyl-1,3,5-hexatriene, *J. Am. Chem. Soc.*, 114, 3607–3612, 1992.
9. For reviews see (a) Scheck, Yu. B., Kovalenko, N. P., Alfimov, M. V. *J. Lumin.*, 15, 157–168, 1977. (b) Fischer, E., Emission spectroscopy evidence for the existence of rotamers in solutions of trans-diarylethylenes and related compounds, *J. Photochem.*, 17, 331–340, 1981. (c) Mazzucato, U. and Momicchioli, F., Rotational isomerism in trans-1,2-diarylethylenes, *Chem. Rev.*, 91, 1679–1719, 1991.
10. Saltiel, J., Sears, Jr., D. F., Choi, J.-O., Sun, Y.-P. and Eaker, D. W., The fluorescence, fluorescence-excitation and UV absorption spectra of trans-1-(2-naphthyl)-2-phenylethene conformers, *J. Phys. Chem.*, 98, 35–46, 1994.
11. Saltiel, J., Tarkalanov, N. and Sears, Jr., D. F., Conformer specific adiabatic cis to trans photoisomerization of cis-1-(2-naphthyl)-2-phenylethene. A striking application of the NEER principle, *J. Am. Chem. Soc.*, 117, 5586–5587, 1995.
12. Saltiel, J., Zhang, Y. and Sears, Jr., D. F., Temperature dependence of the photoisomerization of cis-1-(2-anthryl)-2-phenylethene. Conformer-specificity. torsional energetics and mechanism, *J. Am. Chem. Soc.*, 119, 11202–11210, 1997.
13. See the following reviews and references cited therein: (a) Muszkat, K. A., The 4a,4b-dihydrophenanthrenes, *Topics Curr. Chem.*, 88, 89–144, 1980. (b) Mallory, F. B. and Mallory, C. W., Photocyclization of stilbene and related molecules, *Org. React.* 30, 1–456, 1984. (c) Laarhoven, W. H., 4n+2 Systems. Molecules derived from Z-hexa-1,3,5-triene/cyclohexa-1,3-diene, In *Photochromism, Molecules and Systems*, H. Dürr and H. Bouas-Laurent, Eds., Elsevier, Amsterdam, 1990, 270–313.
14. Laarhoven, W. H., Cuppen, Th. J. H. M. and Nivard, R. J. F., Photodehydrocyclizations in stilbene-like compounds-III; Effect of steric factors, *Tetrahedron*, 26, 4865–4881, 1970.
15. (a) Cherkasov, A. S. *Dokl. Acad. Sci. USSR*, 146, 852, 1962. (b) Cherkasov, A. S., Voldaykina, K. G. *Bull. Acad. Sci. USSR Ser. Phys.* 27, 628, 1963.
16. For a review see Tatsuo, A. and Tokumaru, K., Photochemical one-way adiabatic isomerization of aromatic olefins, *Chem. Rev.*, 93, 23–39, 1993.
17. (a) Brearly, A. M., Strandjord, A. J. G., Flom, S. R. and Barbara, P. F., Picosecond time-resolved emission spectra: techniques and examples, *Chem. Phys. Lett.* 113, 43–48, 1985. (b) Flom, S. R., Nagarajan, V. and Barbara, P. F., Dynamic solvent effects on large-amplitude isomerization rates. 1. 2-Vinylanthracene, *J. Phys. Chem.* 90, 2085–2092, 1986. (c) Brearly, A. M., Flom, S. R., Nagarajan, V. and Barbara, P. F., Dynamic solvent effects on large-amplitude isomerization rates. 2. 2-(2'-Propenyl)anthracene and (E)-2-(but-2'-en-2'-yl)anthracene, *J. Phys. Chem.* 90, 2092–2099, 1986. (d) Barbara, P. F. and Jarzeba, W., Dynamic solvent effects on polar and nonpolar isomerizations, *Acc. Chem. Res.* 21, 195–199, 1988.
18. Determination of the deuterium isotope effect on this [1,7]-sigmatropic shift is reported in Curtin, M. L. and Okamura, M. H., 1α,25-Dihydroxyprevitamin $D_3$: Synthesis of the 9,14,19,19,19-pentadeuterio derivative and a kinetic study of its [1,7]-sigmatropic shift to 1α,25-dihydroxyprevitamin $D_3$, *J. Am. Chem. Soc.*, 113, 6958–6966, 1991.
19. (a) Dauben, W. G. and Phillips, R. B., Effects of wavelength on the photochemistry of provitamin $D_3$, *J. Am. Chem. Soc.*, 104, 5780–5781, 1982. (b) Dauben, W. G., Share, P. E. and Ollmann, R. R., Jr., Triene photophysics and photochemistry: previtamin $D_3$, *J. Am. Chem. Soc.*, 110, 2548–2554, 1988.
20. Dauben, W. G., Disanayaka, B., Funhoff, D. J. H., Kohler, B. E., Schilke, D. E. and Zhou, B., Polyene $2^1A_g$ and $1^1B_u$ states and the photochemistry of previtamin $D_3$, *J. Am. Chem. Soc.*, 113, 8367–8374, 1991.

21. Jacobs, H. J. C., Gielen, J. W. J. and Havinga, E., Effects of wavelength and conformation on the photochemistry of vitamin D and related conjugated trienes, *Tetrahedron Lett.*, 22, 4013–4016, 1981.
22. Kobayashi, T. and Yasamura, M., Studies on the ultraviolet irradiation of provitamin D and its related compounds III. Effect of wavelength on the formation of potential vitamin D2 in the irradiation of ergosterol by monochromatic ultraviolet rays, *J. Nutr. Sci. Vitaminol.*, 19, 123, 1973.
23. Havinga, E., de Kock, R. J. and Rappoldt, M. P., The photochemical interconversions of provitamin D, lumisterol, previtamin D and tachysterol, *Tetrahedron*, 11, 276–284, 1960.
24. Braun, M., Fuβ, W., Kompa, K. L., Wolfrum, J., Improved photosynthesis of previtamin D by wavelengths of 280–300 nm, *J. Photochem. Photobiol. A: Chem.*, 61, 15–26, 1991.
25. Hilinski, E. F., McGowan, W. M., Sears, D. F., Jr. and Saltiel, J., Evolutions of singlet excited-state absorption and fluorescence of all-trans-1,6-diphenyl-1,3,5-hexatriene in the picosecond time domain, *J. Phys. Chem.*, 100, 3308–3311, 1996.
26. Yee, W. A.; O'Neil, R. H., Lewis, J. W., Zhang, J. Z. and Kliger, D. S., Femtosecond transient absorption studies of diphenylpolyenes. Direct detection of $S_2 \rightarrow S_1$ radiationless conversion in diphenylhexatriene and diphenyloctatetraene, *Chem. Phys. Lett.*, 276, 430–434, 1997.
27. Fuβ, W., Lochbrunner, S., The wavelength dependence of the photochemistry of previtamin D, *J. Photochem. Photobiol. A: Chem.*, 105, 159–164, 1997.
28. (a) Maessen, P. A., Jacobs, H. J. C., Cornelisse, J. and Havinga, E., Photochemistry of previtamin $D_3$ at 92 K: Formation of an unstable tachysterol$_3$ rotamer, *Angew. Chem. Int. Ed. Engl.*, 22, 718–719, 1983; (b) Maessen, P. A., Jacobs, H. J. C., Cornelisse, J. and Havinga, E., Photochemistry of previtamin D at 92 K. Formation of an unstable tachysterol rotamer, *Angew. Chem. Suppl.*, 994–1004, 1983. (c) Maessen, P. A. Ph. D. Thesis, Leiden, 1983. (d) Jacobs, H. J. C., Photochemistry of conjugated trienes: Vitamin D revisited, *Pure Appl. Chem.*, 67, 63–70, 1995.
29. Dmitrenko, O., Frederick, J. H., Reischl, W., Previtamin D conformations and the wavelength-dependent photoconversions of previtamin D, *J. Photochem. Photobiol. A: Chem.*, 139, 125–131, 2001.
30. Squillacote, M. E., Semple, T. C., Mui, P. W., The geometries of the high-energy conformers of some acyclic 1,3-dienes, *J. Am. Chem. Soc.*, 107, 6842–6846, 1985.
31. Squillacote, M. E., Sheridan, R. S., Chapman, O. L., Anet, F. A. L., Planar s-cis-1,3-butadiene, *J. Am. Chem. Soc.*, 101, 3657–3658, 1979.
32. (a) Ackerman, J. R., Kohler, B. E., s-cis-Octatetraene: Ground state barrier for s-cis to s-trans isomerization, *J. Chem. Phys.*, 80, 45, 1984. (b) Ackerman, J. R., Forman, S. A., Hossain, M. and Kohler, B. E., s-cis-Octatetraene: Photoproduction and spectroscopic properties, *J. Chem. Phys.*, 80, 3944, 1984.
33. Kohler, B. E., Octatetraene photoisomerization, *Chem. Rev.*, 93, 41–54, 1993, and references cited.
34. Müller, A. M., Lochbrunner, S., Schmid, W. E., Fuβ, W. *Angew. Chem. Int. Ed. Engl.*, 37, 505–507, 1998.
35. Liu, R. S. H.; Asato, A. E. *Proc. Natl. Acad. Sci. U.S.A.*, 82, 259–263, 1985.
36. (a) Liu, R. S. H.; Hammond, G. S. *Proc. Natl. Acad. Sci. U.S.A.*, 97, 11153–11158, 2000. (b) Liu, R. S. H. *Acc. Chem. Res.*, 34, 555–562, 2001.
37. Dauben, W. G., Funhoff, D. J. H. *J. Org. Chem.*, 53, 5070–5075, 1988.
38. Dmitrenko, O., Reischl, W. *Monatsh. Chem.*, 127, 445–453, 1996.
39. Martinez-Nunez, E., Vazquez, S. A., Mosquera, R. A. *J. Comput. Chem.*, 18, 1647–1655, 1997.
40. Cholinski, J., Kutner, A. *Polish J. Chem.*, 71, 1321–1328, 1997.
41. Dmitrenko, O., Frederick, J. H., Reischl, W. *J. Mol. Struct. (Theochem.)*, 530, 85–96, 2000 and references therein.
42. Fuβ, W., Lochbrunner, S., Schmid, W. E., Kompa, K. L. *J. Phys. Chem. A*, 102, 9334–9344, 1998.
43. Fuβ, W., Schmid, W. E., Trushin, S. A. *J. Chem. Phys.*, 112, 8347–8362, 2000.
44. For a recent review of polyene photophysics see Fuβ, W., Haas, Y., Zilberg, S. *Chem. Phys.*, 259, 273–295, 2000.
45. (a) Pullen, S. H., Anderson, N. A., Walker II, L. A., Sension, R. J. *J. Chem. Phys.* 108, 556, 1998. (b) Anderson, N. A., Shiang, J. J., Sension, R. J. *J. Phys. Chem. A*, 103, 10730–10736, 1999.
46. (a) Tarkalanov, N. D. Ph.D. Dissertation, Florida State University, Tallahassee, Fla., 2001. (b) Saltiel, J., Krishnamoorthy, V. Unpublished results.
47. Braun, A. M., Maurette, M.-T., Oliveros, E. *Photochemical Technology*, Wiley, Chichester, 1991, 500–523.
48. Saltiel, J., Cires, L. Unpublished observations.
49. For a review see Saltiel, J., Sun, Y.-P. In *Photochromism, Molecules and Systems*, Dürr, H. Bouas-Laurent, H. Eds., Elsevier, Amsterdam, 1990, 64–164.
50. Sklar, S. K., Hudson, B., Petersen, M., Diamond, J. *Biochem.*, 16, 813–828, 1977.
51. (a) Zimányi, L., Kulcsár, Á., Lanyi, J. K., Sears, D. F., Jr., Saltiel, J. *Proc. Natl. Acad. Sci. USA*, 96, 4408–4413, 1999. (b) Zimányi, L., Kulcsár, Á., Lanyi, J. K., Sears, D. F., Jr., Saltiel, J. *Proc. Natl. Acad. Sci. USA*, 96, 4414–4419, 1999.
52. Alfimov, M. V., Gromov, S. P., Fedorov, Y. V., Fedorova, O. A., Vedernikov, A. I., Churakov, V., Kuz'mina, L G., Howard, J. A. K., Bossmann, S., Braun, A., Woerner, M., Sears, Jr., D. F., Saltiel, J. *J. Am. Chem. Soc.*, 121, 4992–5000, 1999.
53. Jacobs, H. J. C., Gielen, J. W. J., Havinga, E. *Tetrahedron Lett.*, 22, 4013, 1981.
54. Reichenbächer, M., Gliesing, S., Lange, C., Gonschlor, M., Schönecker, B. *J. pract. Chem.*, 338, 634–641, 1996.
55. Malatesta, V., Willis, C., Hackett, P. A. *J. Am. Chem. Soc.*, 103, 6781–6783, 1981.
56. Dauben, W. G., Phillips, R. B. *J. Am. Chem. Soc.*, 104, 355–356, 1982.
57. (a) Sanders, G. M., Pot, J. Havinga, E., Some recent results in the chemistry and stereochemistry of vitamin D and its isomers, *Prog. Chem. Org. Natl. Prod.*, 27, 131–157, 1969.
58. (a) Boomsma, F., Jacobs, H. J. C., Havinga, E., van der Gen, A. The "over irradiation products" of previtamin D and tachysterol: toxisterols, *Recl. Trav. Chim.*, 96, 104, 1977. (b) Boomsma, F., Jacobs, H. J. C., Havinga, E., van der Gen, A. The photochemistry of previtamin D and tachysterol, *Rec. Trav. Chim.*, 96, 113, 1977.
59. Snoeren, A. E. C., Daha, M. R., Lugtenburg, J. Havinga, E. *Recl. Trav. Chim.*, 89, 261–264, 1970.
60. Eyley, S. C., Williams, D. H. *J. Chem. Soc. Chem. Commun.* 858, 1975.
61. Denny, M., Liu, R. S. H. *Nouv. J. Chem.*, 2, 637–641, 1978.
62. Stevens, R. D. S. U.S. Pat. No. 4,686,023, 1987.

63. Pfoertner, K.-H. *J. Chem. Soc, Perkin Trans.* 2, 523–526, 1991.
64. Pfoertner, K.-H. *J. Chem. Soc, Perkin Trans.* 2, 527–530, 1991.
65. Tatikolov, A. S., Dmitrenko, O., Terenetskaya, L. P. *Chem. Phys. Reports,* 14, 461–466, 1995.
66. (a) Hammond, G. S., Saltiel, J., Lamola, A. A., Turro, N. J., Bradshaw, J. S., Cowan, D. O., Counsell, R. C., Vogt, V., Dalton, C. J. *Am. Chem. Soc.,* 86, 3197–3217, 1964. (b) Saltiel, J., Charlton, J. L. In *Rearrangements in Ground and Excited States*, de Mayo, p., Ed., Academic Press, New York, Vol 111, 25–89, 1980.
67. Nowakowska, M., Foyle, V. P., Guillet, J. E. *J. Am. Chem. Soc.,* 115, 5975–5981, 1993.
68. Nowakowska, M., Guillet, J. E. *J. Photochem. Photobiol. A: Chem.* 107, 189–194, 1997.
69. (a) Liu, R. S. H., Butt, Y. C. C. *J. Am. Chem. Soc.,* 93, 1532–5981, 1971. (b) Liu, R. S. H. *Pure Appl. Chem., Supplement,* 335–350, 1971. (c) Butt, Y. C. C., Singh, A. K., Baretz, B. H., Liu, R. S. H. *J. Phys. Chem.,* 85, 2091, 1981.
70. Møller, S., Langkilde, F. W., Wilbrandt, R. *J. Photochem. Photobiol. A: Chem.* 62, 93–106, 1991.
71. (a) Saltiel, J., Wang, S., Ko, D.-H., Gormin, D. A. *J Phys Chem. A.,* 102, 5383–5392, 1998. (b) Saltiel, J., Crowder, J. M., Wang, S. *J. Am. Chem. Soc.,* 121, 895–902, 5352, 1999.

BACKGROUND OF THE INVENTION

Photochemistry in the vitamin D field has played a central role in the development of molecular photochemistry. Especially noteworthy have been the early contributions of Havinga[1] and of Dauben[2] and their coworkers. Havinga's principle of the nonequilibration of excited rotamers (NEER) was introduced to explain the excitation wavelength dependence of the photoproducts of the trienes previtamin D and tachysterol, Scheme 1.[3] The NEER principle was based on the idea, inspired by Hückel MO theory, that excitation of conjugated polyenes and related molecules to their lowest singlet or triplet excited states tends to reverse double/single bond character preventing equilibration of ground state conformers. Thus, the ground state conformer equilibrium compositions, the individual spectra and excited state energies of the conformers and the conformer-specific photochemical properties of the conformers control observed product quantum yields and distributions. The dependence of acyclic 1,3-diene photodimer distributions[4] and trans/cis photostationary states[5,6] on the triplet excitation energy of the sensitizer demonstrated by Hammond and coworkers, soon thereafter, provided dramatic confirmation of this principle, FIG. 1 and Schemes 2 and 3. Ground state conformer controlled photochemical ring opening of a substituted 1,3-cyclohexadiene to isomeric conjugated trienes was first reported in the case of α-phellandrene, Scheme 4.[7]

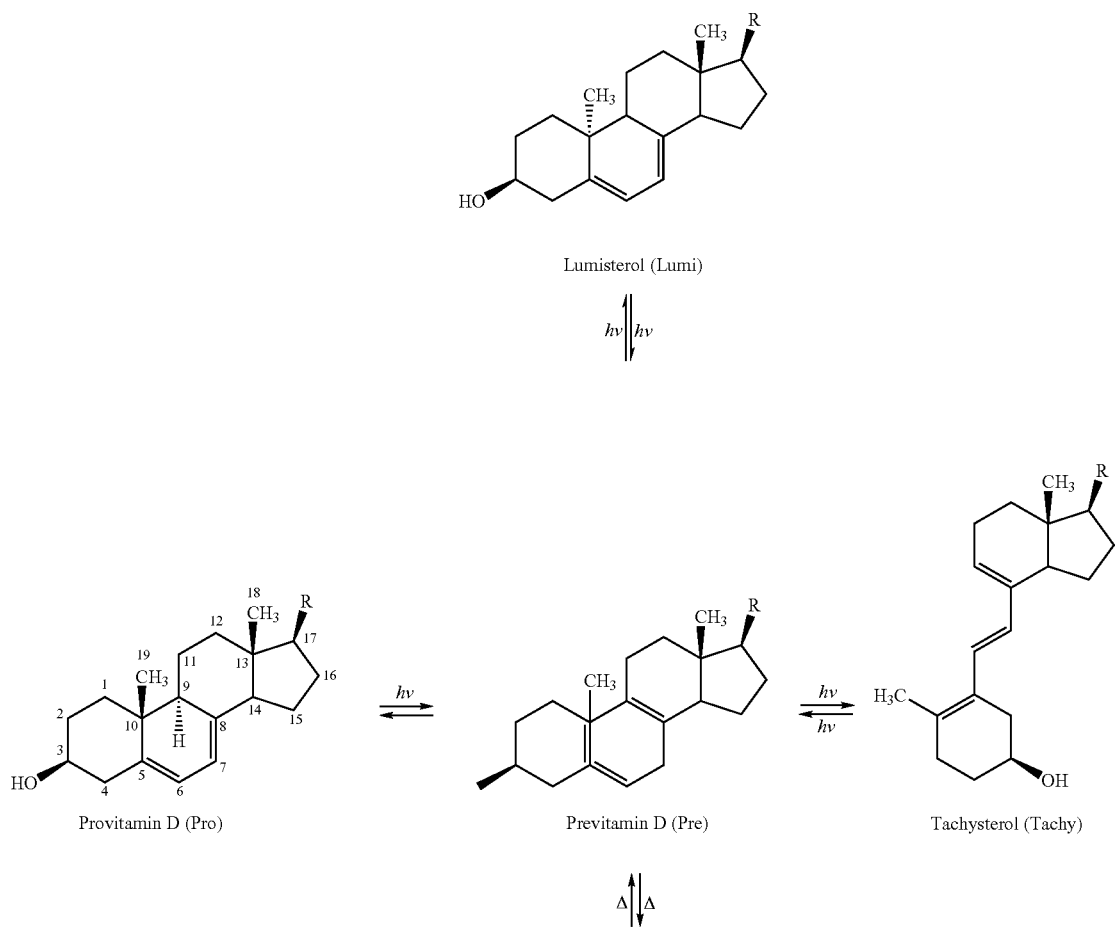

Scheme 1. Major photochemical events in the vitamin D field.

-continued
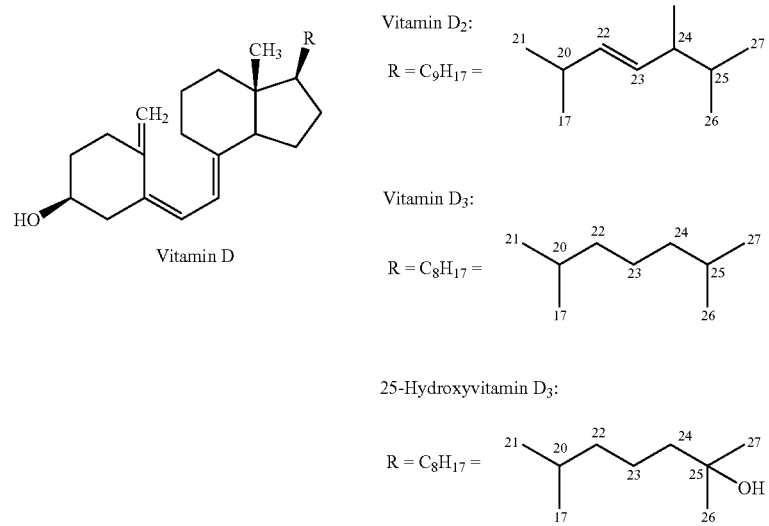
Scheme 2. Fluorenone-sensitized 1,3-butadiene dimerization.
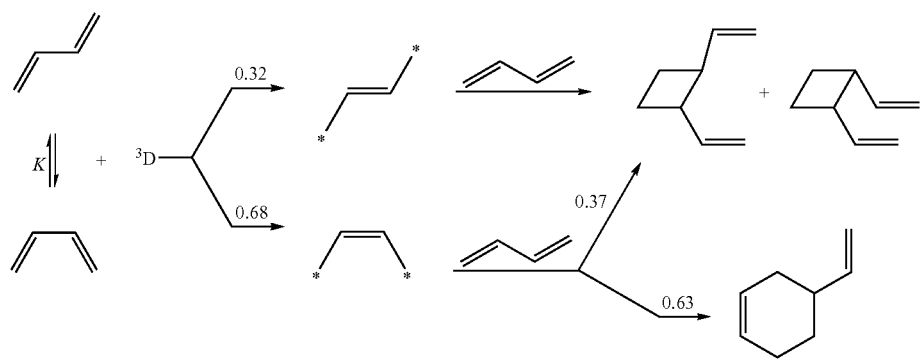
Scheme 3. Fluorenone-sensitized isomerization of trans,trans-2,4-hexadiene.
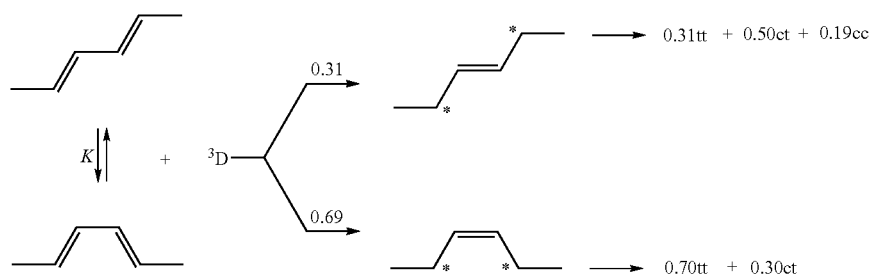

Scheme 4. Conformer specific ring opening of α-phellandrene.

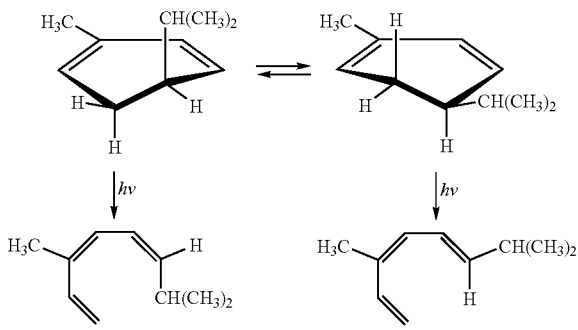

Demonstrations of photophysical manifestations of NEER include the resolution of the fluorescence of all-trans-1,6-diphenyl-1,3,5-hexatriene into s-trans,s-trans and s-cis,s-trans contributions[8] and analogous resolutions of fluorescence and absorption spectra of styrylarene conformers.[9,10] The conformer-specific adiabatic cis⇒trans photoisomerizations of 2-styrylnaphthalene[11] (cis- and trans-NPE) and 2-styrylanthracene[12] are especially striking examples. In each case, the more extended s-trans-like conformer undergoes adiabatic cis⇒trans photoisomerization whereas the less extended s-cis-like conformer undergoes selective photocyclization, Scheme 5.[13,14] In this sense, these cis-diarylethenes can be regarded as true previtamin D mimics.

In recent years, it has been suggested that not all the excitation wavelength dependence of quantum yields in the vitamin D field can be accounted for by the NEER principle. Below are considered the competing mechanisms that have been proposed to account for photochemical observations and describe some of the strategies that have been employed to improve the photochemical production of the previtamins from the provitamins. Optimization of the previtamin yields improves vitamin yields as the latter are formed thermally from the previtamins via 1,7-suprafacial hydrogen shifts.[18] Readers interested in the rich photochemistry leading to over-irradiation products should consult previous reviews.[1a,2b]

Mechanism

Paradoxically, it was the dependence of product distributions and quantum yields in the interconversion of vitamin D precursors on the excitation wavelength that led Havinga to the postulation of the NEER principle and it was, subsequently, systematic confirmation of such dependence that led Dauben, Kohler and coworkers and, more recently, Fuβ and coworkers to propose alternative explanations.

The experimental data that have been presumed to be incompatible with the NEER principle derive from studies by Dauben and coworkers of the $\lambda_{exc}$ dependencies of cis-trans photoisomerization (to tachysterol, $\phi_T$ and photocyclization quantum yields (to provitamin $D_3$ and lumisterol, $\phi_{PRO}$ and $\phi_{LUMI}$, respectively) starting from pure previtamin Scheme 5. Conformer specific photochemistry of c-NPE.

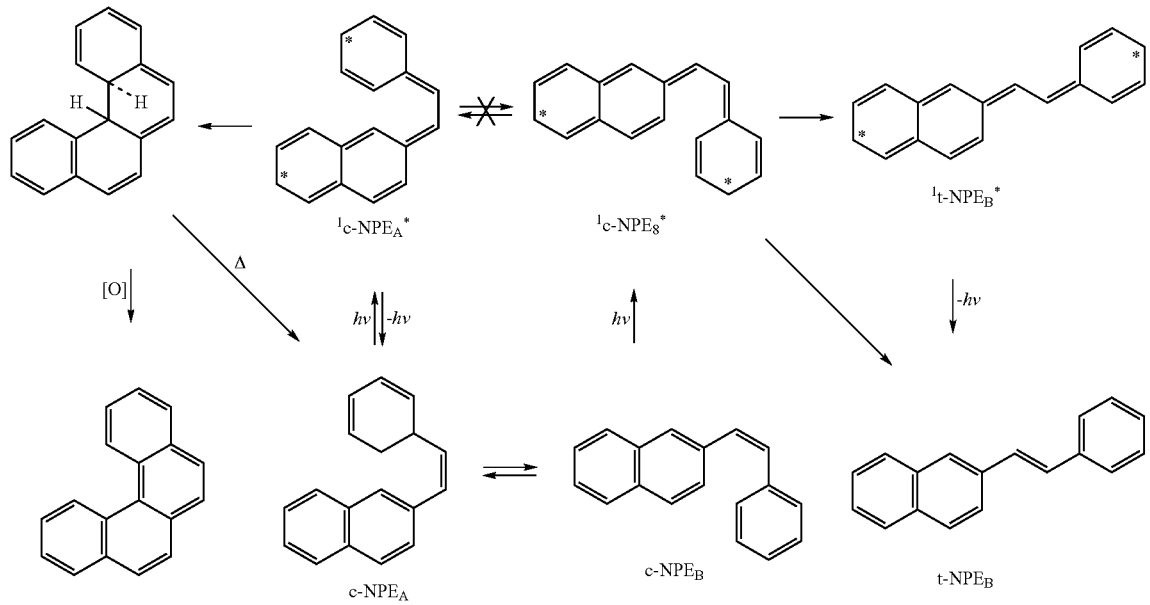

Adherence to the NEER principle is expected in molecules with relatively short-lived excited states in which the electronic excitation is delocalized extensively over the conjugated Π-system. In such molecules torsional barriers about essential ground state single bonds are enhanced in the lowest excited states. Conversely, molecules that have long excited state lifetimes and in which there is pronounced localization of electronic excitation in parts of the Π-system are likely to violate the NEER principle. Alkenyl-substituted anthracenes provide well-documented examples.[9,15-17]

$D_3$.[19,20] Quantum yields were measured in ref 20 (de-aerated anhydrous diethyl ether, 0° C.). In ref 19 relative quantum yields were estimated from quasi-photostationary states and molar absorptivities and were converted to absolute quantum yields on the basis of Havinga's measurements at 254 and 302.5 nm.[21] Photocyclization quantum yields ($\phi_{PRO}$+ $\phi_{LUMI}$) increase and photoisomerization quantum yields ($\phi_T$) decrease as $\lambda_{exc}$ is increased, FIG. 2. A study of the effect of $\lambda_{exc}$ in the 225–400 nm range on the formation of "potential vitamin $D_2$" had found 295-nm light to be most effective,[22]

in good agreement with the earlier findings of Havinga and coworkers[23] and a more recent study by Braun et al.[24] The "sudden" increase in the photocyclization quantum yields and decrease in the photoisomerization quantum yields in the narrow 302–305 nm $\lambda_{exc}$ range ($\phi_{PRO}$=0.02, 0.04, $\phi_{LUMI}$=0.07, 0.13 and $\phi_T$=0.31, 0.27 for 302 and 306 nm, respectively[20]) was judged to be inconsistent with changes in the absorption spectra of the previtamin conformers, potential specific precursors of the three photoproducts, Scheme 6.[19,20] It was suggested that $\lambda_{exc}$≦302 nm populates the lowest allowed 1B or $S_2$ excited state of the previtamin which major reaction channel, photoisomerization, competes with internal conversion to $S_1$, the lowest (doubly) excited singlet state 2A. Excitation at longer wavelengths, $\lambda_{exc}^3$≧304 nm, directly populates $S_1$ whose major reaction channel, photocyclization, competes with radiationless decay to $S_0$, FIG. 3.[19,20] This interpretation was bolstered by low temperature (77 K) fluorescence measurements assigned to the $S_1$⇒$S_0$ transition in the previtamin that appeared to gain dramatically in intensity for $\lambda_{exc}$>300 nm.[20] The latter result suggests poor communication between $S_2$ and $S_1$ excited states in contrast to the very rapid $S_2$⇒$S_1$ in all-trans-1,6-diphenyl-1,3,5-hexatriene.[25,26] However, the relevance of the low temperature spectroscopic observations in a rigid medium to the interpretation of the high temperature photochemical observations in solution is questionable because different conformer equilibrium distributions are likely to be involved (see below).

Fuβ and Lochbrunner have advanced an alternative interpretation of the $\lambda_{exc}$ dependence of the quantum yields in FIG. 2.[27] They retain Havinga's ground state conformer control at $\lambda_{exc}$≦302 nm, but propose that the jumps in the quantum yields over the narrow wavelength range that follow are due to competing barrierless photocyclization and activated photoisomerization pathways in cZc-previtamin. Because of the short excited state lifetime, photoisomerization competes with vibrational relaxation, such that excitation over the torsional barrier favors cis⇒trans photoisomerization as a hot excited state reaction, FIG. 4. Common features of the mechanisms in FIGS. 3 and 4 are that they attribute the sharp change in the quantum yields to the behavior of the excited states of a single conformer. Enhanced cis⇒trans photoisomerization efficiency with wavelengths shorter than 302 nm is assigned to the 1B state of the cZc (s-cis at $C_5C_6$, cis at $C_6C_7$ and s-cis at $C_7C_8$) conformer in the Dauben/Kohler mechanism and to a vibrationally hot $S_1$ (presumably 2A) state in the Fuβ mechanism. Fuβ argues in favor of his mechanism because it accounts for the monotonic increase in the overall cyclization quantum yield at the longer wavelengths that populate only $S_1$, whereas a constant quantum yield would be expected from the Dauben/Kohler mechanism.[27] However, the argument is not compelling because neither mechanism takes into account the fact that provitamin (Pro) and lumisterol (Lumi) have different (at least in a helical sense) cZc-previtamin (cZc-Pre) precursors. Thus, consideration of observed and Scheme 6. Conformer specific photochemistry of Pre in solution.

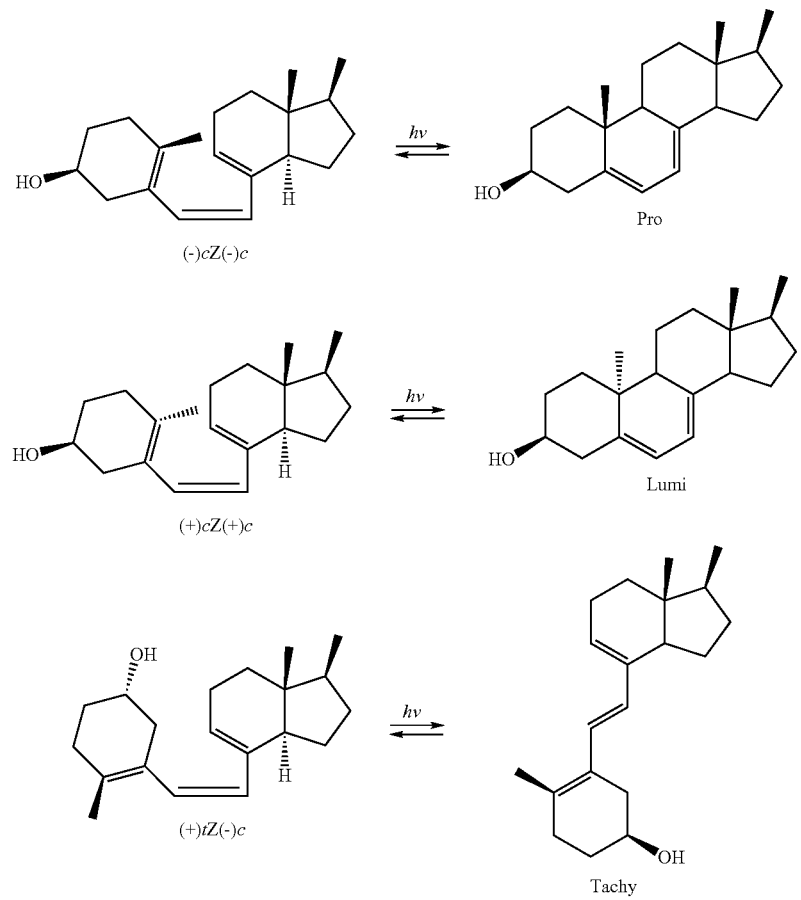

expected changes in the spectra of the conformers of the previtamin indicates that the NEER principle still provides a viable explanation for the quantum yield variation in FIG. 2,[28c] accounting also for the change in the $\phi_{LUMI}/\phi^{PRO}$ ratio.[29]

What is then the relationship between photoisomerization and photocyclization quantum yields that would be predicted if the NEER principle were adhered to strictly throughout the $\lambda_{exc}$ range? In view of the structural requirements of the two reactions, it is assumed that only cZc conformers undergo photocyclization and that the rest undergo only photoisomerization. For simplicity, it is also assumed that the cis→trans photoisomerization quantum yields of the cZc conformers are relatively small and can be neglected (this is not an essential assumption). Using the notation adopted by Fuβ,[27] the previtamin conformers are divided into a set P that photoisomerizes and a set $P_0$ that photocyclizes. Since the sum $\phi_T+\phi_{PRO}+\phi_{LUMI}$ starts at 0.48 at the shorter wavelengths where $\phi_T$ dominates and decreases to 0.44 at the longer wavelengths where $\phi_{PRO}$ and $\phi_{LUMI}$ dominate (these are minimum values since back reaction corrections were not applied),[20] it is reasonable to assume maximum quantum yields of 0.50 and 0.40 for the photoisomerization of the P conformer set and the photocyclization of the $P_0$ conformer set, respectively, independent of $\lambda_{exc}$. It follows that the fraction of absorbed light that excites P conformers is $\phi_P=\phi_T/0.50$, and the remainder, $\phi_{P0}=(1-\phi_P)$, is the fraction that excites $P_0$ conformers. This allows calculation of the sum of cyclization quantum yields from the photoisomerization quantum yields: $(\phi_{PRO}+\phi_{LUMI})=0.40(1-\phi_P)$. Cyclization quantum yields obtained in this way, FIG. 2, are in excellent agreement with observed values at short and long wavelengths. The quantum yield "jump" is reproduced satisfactorily, but is predicted to occur at shorter wavelengths by about 2 nm in better agreement with results from the earlier study.[19] Application of this procedure separately on the experimental $\phi_{PRO}$ and $\phi_{LUMI}$ values can be used to divide $\phi_{P0}$ into excitation fractions of cZc conformers that differ in helicity. In view of the large number of potentially accessible conformers and the low absorbance of the system above 300 nm, (see below) a 2 nm lag between the fall in $f_T$ and the rise in $(\phi_{PRO}+\phi_{LUMI})$ could be caused by the drop of tZc conformer absorption initially coinciding with competing absorption by conformers that have low photoisomerization and photocyclization efficiencies. Clearly, the NEER principle accounts for the data over the entire wavelength range and predicts that absorption by the $P_0$ conformer set is shifted to the red of the absorption of the P conformer set, becoming important at the onset of the previtamin D spectrum (see below).

The production of vitamin Ds provides a rare example of an industrial scale synthesis in which, free radical chain reactions aside, photochemistry in vitro plays a crucial role.[47]

Three strategies have been proposed in order to maximize the photochemical yields of Pre. They all have in common as a first step, roughly monochromatic UV-excitation of Pro in the absence of oxygen with the goal of approaching quasi-photostationary states (Q-PSS), Scheme 1. Over-irradiation, or even attainment of the Q-PSS is avoided because of slow, irreversible stoichiometric losses of the interconverting isomers to undesirable isomers, transparent to the exciting light.[1,2] The success of the first strategy depends on the selection of an excitation wavelength that yields the largest previtamin contribution in the Q-PSS and employs no other photochemical step in the synthesis.[22-24] The optimum $\lambda_{exc}$ selection has been based on the quantum yields of the interconversions and the absorption spectra of the contributing isomers. There is a general shift of the $I_{max}$ of the absorption spectra to the red with increasing solvent polarizability $a=(n^2-1)/(n^2+2)$, where n is the index of refraction,[48] similar to that experienced by the a,w-diphenylpolyenes,[49,50] and more subtle changes are expected at the onset due to the influence of solvent on the equilibrium distribution of the conformers.[28] FIG. 7 shows the polarizability effect on the spectra of the Pro and Pre 25-OH analogues of vitamin $D_3$ (HOVit$_3$).[48] The effect is generally more pronounced for the trienes than for the cyclohexadienes.[48] The set of spectra for the 25-OH vitamin $D_3$ (HOVit$_3$) isomers in methanol, FIG. 8,[48] is typical.

The other two strategies employ two photochemical steps. The excitation wavelength in the first step is chosen so as to maximize the conversion of Pro to Pre and Tachy and a longer excitation wavelength, with or without an added triplet energy donor, is used in the second step to convert the initial Pre and Tachy mixture to a Pre-rich Q-PSS. The proposed sequential direct excitation procedures recommend use of a short wavelength (248 or 254 nm) for the Pro to Pre+Tachy step, followed by a second excitation wavelength in the 337–355 nm range to convert most of the Tachy to Pre.[55,56] These procedures have sought to take advantage of the fact that the Tachy UV spectrum extends to longer wavelengths than the Pre spectrum, FIG. 8. Unfortunately, the second wavelengths that have been suggested are barely absorbed by Tachy and, in addition, the desired selective excitation advantage is almost lost. For instance, the molar absorptivities of Tachy$_3$ and Pre$_3$ at 350 nm in diethyl ether are given as 100 and 25 M$^{-1}$cm$^{-1}$, respectively.[56] To make matters worse, wavelengths longer than 296 nm selectively excite cZc-Pre conformers (probably directly into the 2A state) and favor return to Pro and, especially, formation of Lumi, FIG. 11.[19,20,24] Results from the Dauben and Phillips study are shown in FIG. 12. They show that the Tachy⇒Pre conversion is the dominant process during the initial 350-nm irradiation period and that only when it is nearly complete do the Pre⇒Lumi and Pre⇒Pro photoreactions take over. The irradiation sequence in FIG. 12 yielded up to 83% Pre at 95% Pro conversion.[56] The large Pre/Tachy Q-PSS ratios that were achieved with $\lambda_{exc}$=350 nm indicate that the quantum yield in the Tachy⇒Pre direction is at least four times larger than in the Pre⇒Tachy direction. Since, furthermore, Lumi becomes the major component in the Q-PSS at long irradiation times, it follows that the quantum yield trends in FIG. 2 extend to longer wavelengths.

SUMMARY OF THE INVENTION

With the foregoing in mind, the present invention advantageously provides for a method of improving the photochemical conversion of Pro to Pre, followed by the thermal rearrangement of the latter to the vitamin Ds (Vit). The skilled will recognize that there are several compositions which are included in the family of vitamin Ds, and these are all intended to be included within the scope of the present invention. It is desirable to achieve high conversions to the Pre while reducing yields of the undesirable secondary photoproducts Lumi and Tachy.[1,2] Finally, the thermal Pre-Vit conversion must be carried out at an intermediate temperature in order to avoid competing thermal disrotatory cyclizations to pyro- and isopyrocalciferols, cyclohexadiene stereoisomers of the lumisterols and provitamins with cis ring B junctions, that occur at temperatures above 100° C.[47] The present invention is also summarized in a scientific paper titled Conformer-Specific Photoconversion of 25-Hydroxytachysterol to 25-Hydroxyprevitamin $D_3$: Role in the Production of Vitamin Ds; by Jack Saltiel et al., *J. Am. Chem. Soc.* 2003, 125, 2866–2867; a publication which is incorporated herein by reference in its entirety.

The separation of photochemical and thermal steps is desirable because it prevents formation of Vit photoproducts. The use of the 313 nm Hg line to effect the HOTachy⇒HOPre conversion as an alternative wavelength in the second irradiation step is disclosed herein. This wavelength is absorbed more strongly and more selectively by the Tachy chromophore, FIG. 8. Essentially identical Tachy⇒Pre quantum yields of 0.10 at 254 and 313 nm in diethyl ether were reported by Havinga et al. A similar claim had been made by Dauben and Philips for 254 and 302 nm excitations. In contrast the present invention discloses that at 313 nm the conversion of HOTachy to HOPre is four times more efficient than at 254 nm. The invention shows that the 254, 313 nm two-step sequence, therefore, has advantages over the earlier sequences that employed longer wavelengths in the second step. It achieves high, relatively clean Tachy to Pre conversion without requiring long irradiation times due to low absorbance in the second irradiation step and avoids competing Pre photocyclizations to Pro and Lumi. Most quantitative determinations of the progress of the photochemical conversions, as Q-PSS relationships are approached, have previously been by HPLC analysis, a rather time-consuming method. The availability of an accurate set of absorption spectra, such as those in FIG. 8, allows the product distribution to be conveniently determined directly from UV spectra of the reaction mixture taken during the course of the irradiation.

The shoulder at the onset (330–300 nm) of the HOTachy spectrum suggests that excitation at 313 nm selectively excites a minor conformer, whereas excitation at 254 nm probably excites the more abundant tEc conformer (shown in Scheme 1). A recent molecular mechanics-based (MMX) conformational search confirms the placing of tEc as the most abundant conformer (63%) and predicts cEc (18%) to be slightly more abundant than tEt (13%). The weak structureless band at the onset of the UV spectrum of HOTachy should then be assigned to either the cEc or the tEt conformer with the former more likely since s-cis diene moieties normally absorb at longer wavelengths. Therefore, the Tachy ϕPre quantum yields $\phi_{TP}$ were remeasured. HOTachy, prepared by 254-nm (low-pressure Hg lamp) irradiation of deaerated HOPro in methanol (MeOH), was isolated by preparative HPLC. Degassed methanol solutions in 13-mm o.d. ampules (quartz for 254 and Pyrex for 313 nm) were irradiated in a merry-go-round apparatus at 20° C. Some ampules were provided with sidearms attached to 3-mm UV cells. Analysis of the time evolution of UV spectra by singular value decomposition (SVD) complemented HPLC analysis. The trans-cis photoisomerization of stilbene was used for actinometry, and conversions were corrected for back-reaction. It was found that $\phi_{TP}$=0.12±0.02 at 254 nm as expected, but $\phi_{TP}$=0.42±0.02 at 313 nm, a factor of about 4 times larger than previously reported values ([HOTachy] in the 3.2–9.0×10$^{-4}$ M range). On the basis of predicted conformer energetics and absorption spectra, it follows that cEc-Tachy gives Pre much more efficiently than does tEc-Tachy. The product evolution from a 3-component SVD analysis of UV spectra of a typical run is shown in FIG. 16. It neglects small amounts of HOPro and HOVit present at longer times. HPLC analysis of the final reaction mixture gave 5.7% (6.9) HOTachy, 81.9% (82.4) HOPre, 8.3% (7.8) HOLumi, 2.4% HOPro, and 1.8% HOVit (values in parentheses are from the SVD analysis in FIG. 16). Nearly identical product compositions are reached much faster without the use of the 313-nm filter solution because 313 nm is the only Hg line (medium pressure Hg lamp) transmitted by Pyrex® glass that is significantly absorbed by the mixture, FIG. 8. The large HOPre/HOTachy Q-PSS ratio disagrees with previous expectations. These results explain the Pre $D_3$-rich Q-PSS (59%) that was obtained recently upon 308 nm excitation of 7-dehydrocholesterol (Pro $D_3$) in ethanol. Similar conversions to HOPre were achieved starting from either HOTachy (313 nm) or HOPro (254/313-nm stepwise sequence). In a typical experiment, 4.5×10$^{-4}$ M HOPro in MeOH was irradiated at 254 nm for 300 min to a mixture of 14.8% HOPro, 23.2% HOPre, 59.3% HOTachy, 2.0% HOLumi, and 0.6% HOVit and afterward, at 313 nm for 150 min to a final composition of 11.8% HOPro, 74.3% HOPre, 6.1% HOTachy, 5.4% HOLumi, and 2.4% HOVit (HPLC). UV spectra recorded during the course of these irradiations were treated by SVD as a four-component system (HOVit was neglected). The plot of the combination coefficients of the three major eigenvectors, FIG. 17, is revealing. Points for the experimental spectra fall close to the stoichiometric plane defined by the spectra of the pure components HOPro, HOPre, and HOTachy. Initially, irradiation at 254 nm moves the system from the HOPro corner toward HOPre, but it soon turns toward HOTachy. The switch to 313 nm irradiation causes the sharp turn toward HOPre. The second step of the 254/313 nm two-step sequence achieves high, clean Tachy-to-Pre conversion with minimal competing Pre photocyclizations to Pro and Lumi without requiring high excitation intensities due to the low absorbances at previously used $\lambda_{exc}$.

BRIEF DESCRIPTION OF THE DRAWINGS

Some of the features, advantages, and benefits of the present invention having been stated, others will become apparent as the description proceeds when taken in conjunction with the accompanying drawings, presented solely for exemplary purposes and not with intent to limit the invention thereto, and in which:

FIG. 17 is a graph showing combination coefficients for the two-stage 254/313 nm conversion of HOPro to a HOPre-rich mixture.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Conformer Spectra Energies and Populations

Experimental verifications of the conformational dependence of the UV absorption spectra of the triene moieties in tachysterol ($Tachy_3$) and previtamin $D_3$ ($Pre_3$) were obtained by excitation of $Pre_3$ at 92 K in a rigid EPA' glass[28] (5/5/1 solution of ether/isopentane/ethyl alcohol) and of $Pro_3$ in EPA[27,30] (5/5/2 solution of ether/isopentane/ethyl alcohol), respectively. The current interpretation of these results is due to Fuβ and is shown in Scheme 7.[30]

Scheme 7. Proposed conformer specific Hula-Twist photoisomerization of Pre in a rigid medium.

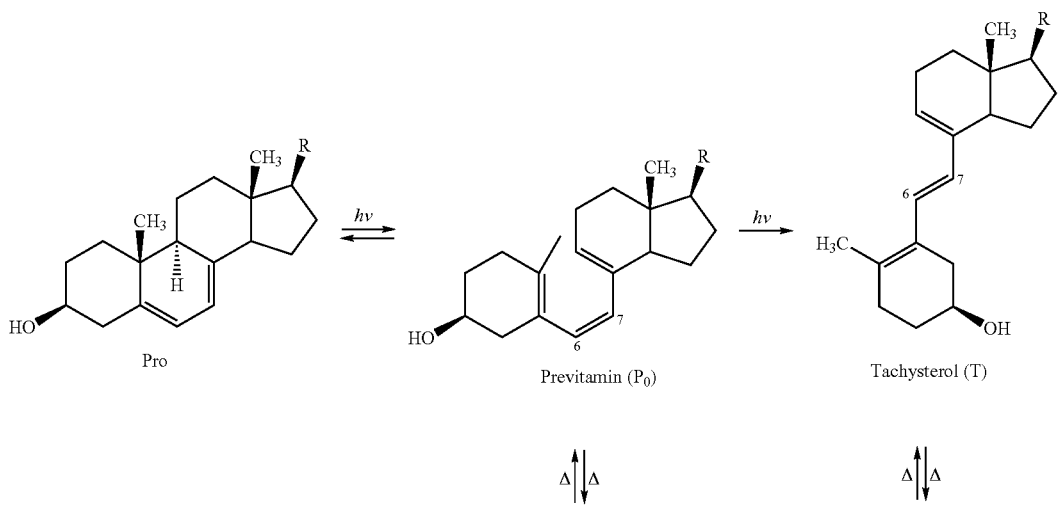

-continued

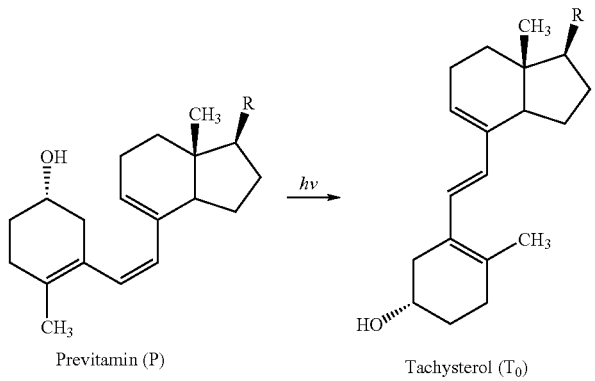

Previtamin (P)      Tachysterol ($T_0$)

Figure 1:
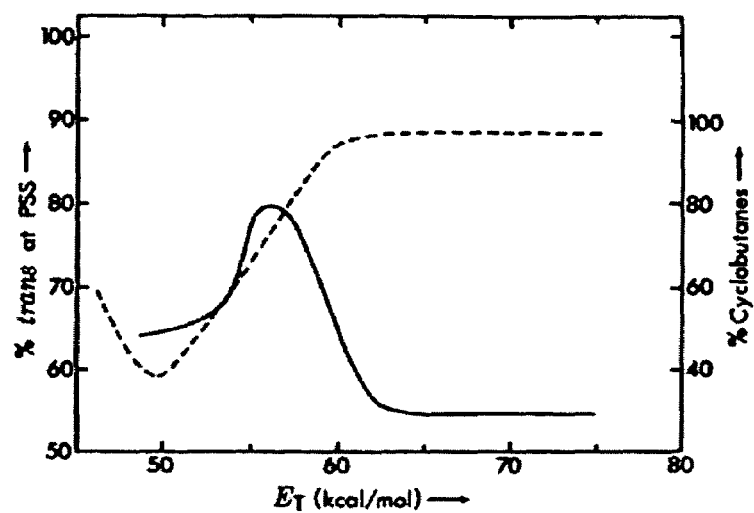
FIG. 1 shows Saltiel plots of 1,3-butadiene dimer compositions (dashed line) and 1,3-pentadiene trans/cis photostationary states as a function of the triplet energy of the sensitizer (reproduced from reference 6)
Figure 2:
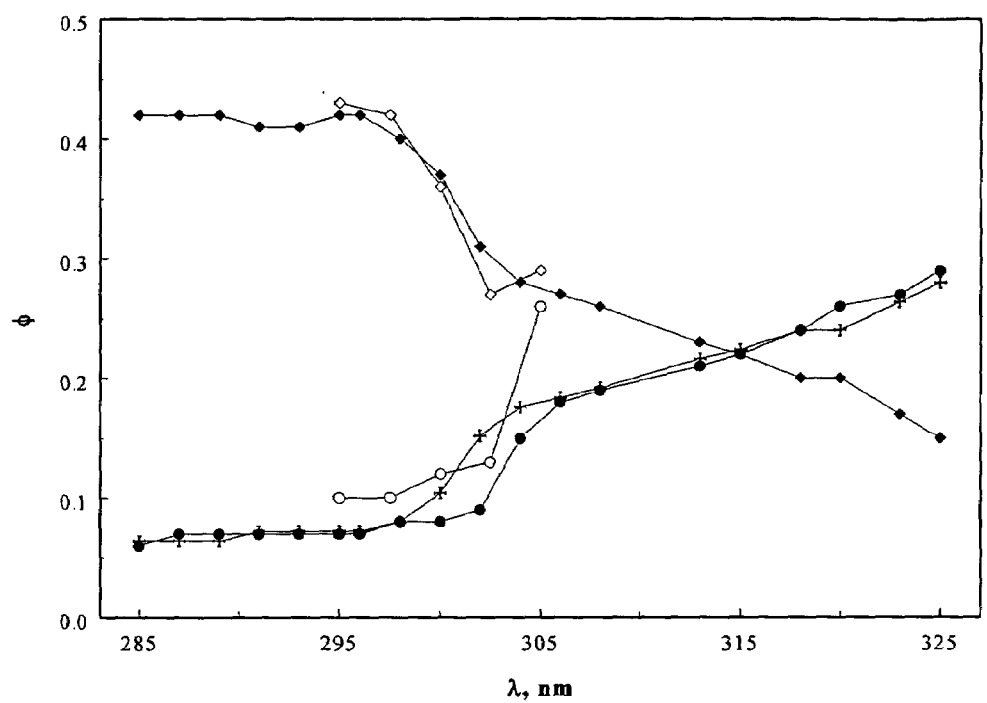
FIG. 2 is a plot of excitation wavelength dependence of photocyclization (○[19b], ●[20]) and photoisomerization (◇[19b], ◆[20]) quantum yields starting from previtamin $D_2$ in ether at 0° C.; crosses designate calculated photocyclization quantum yields based on the NEER principle, see text.he Dauben-Kohler 1B/2A mechanism for cZc-previtamin D photochemistry (reproduced from reference 19b)
Figure 3:
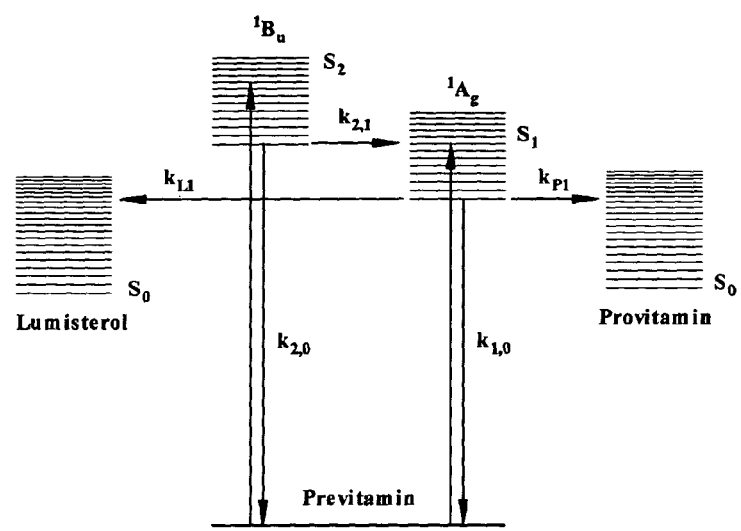
FIG. 3 shows the Fuβ hot excited state mechanism for cZc-previtamin D photochemistry in $S_1$ (2A) (reproduced from reference 27)
Figure 4:
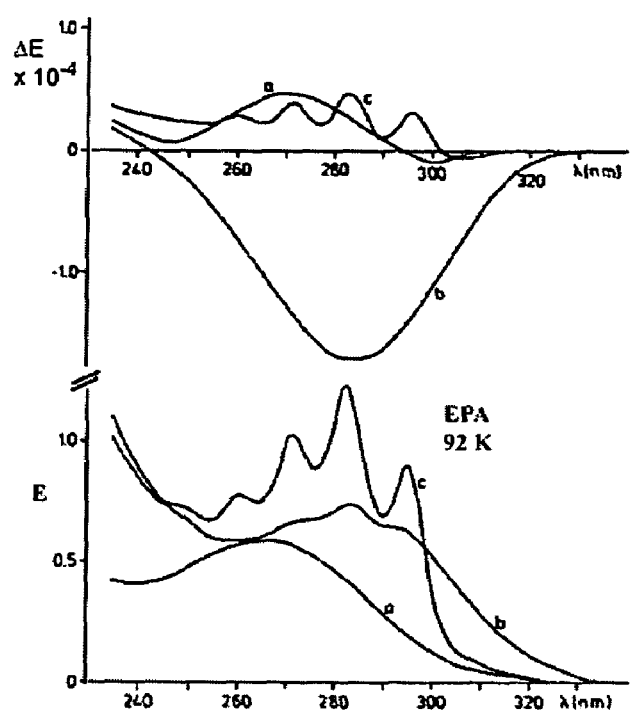
FIG. 4 are UV and CD spectra before (curves a) and after (curves b) irradiation of previtamin $D_3$ in EPA at 92 K. Curves c are for the irradiated sample after it was warmed to 105 K and re-cooled to 92 K (reproduced from reference 28)
Figure 5:
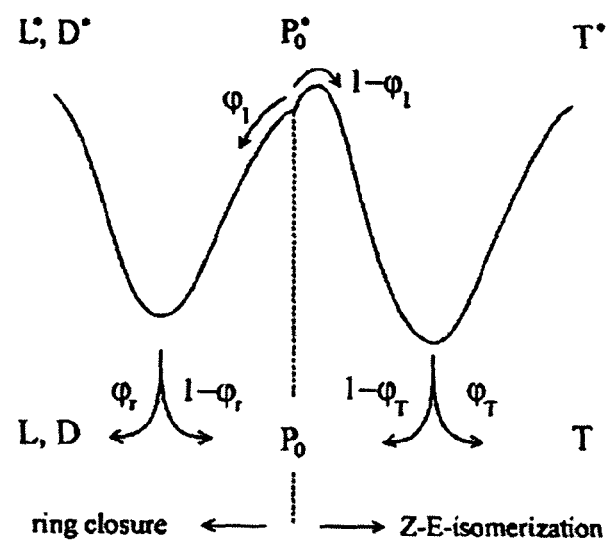
FIG. 5 shows UV and CD spectra before (curves a) and after (curves b) irradiation of previtamin $D_3$ in EPA at 92 K Curves c are for the irradiated sample after it was warmed to 105 K and re-cooled to 92 K (reproduced from reference 28)
Figure 6:
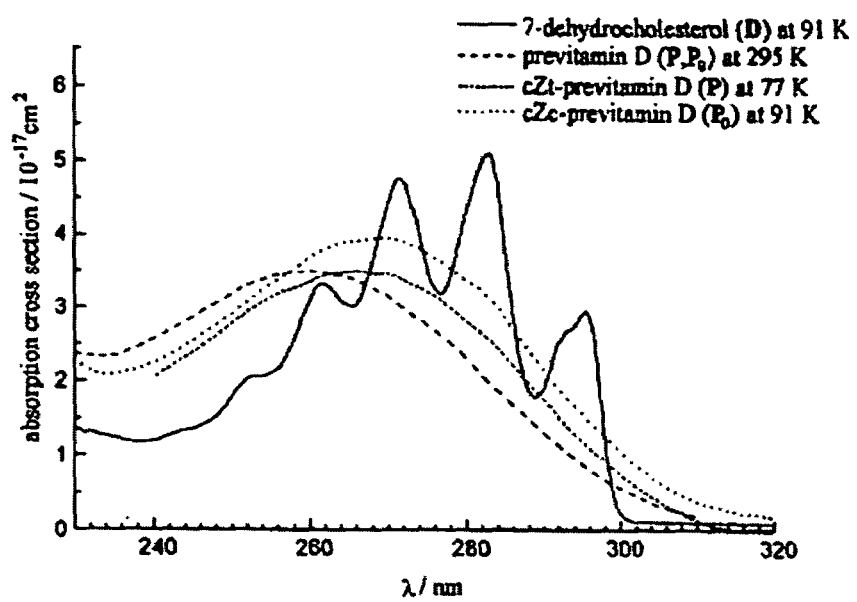
FIG. 6 shows UV spectra of provitamin $D_3$ at 91 K, previtamin $D_3$ at 77 K (designated as conformer set P). previtamin $D_3$ formed in situ from provitamin $D_3$ at 91 K (designated as conformer set $P_0$), and previtamin $D_3$ at 295 K (designated as equilibrium $P_0/P$ conformer mixture; reproduced from reference 27)
Figure 7:
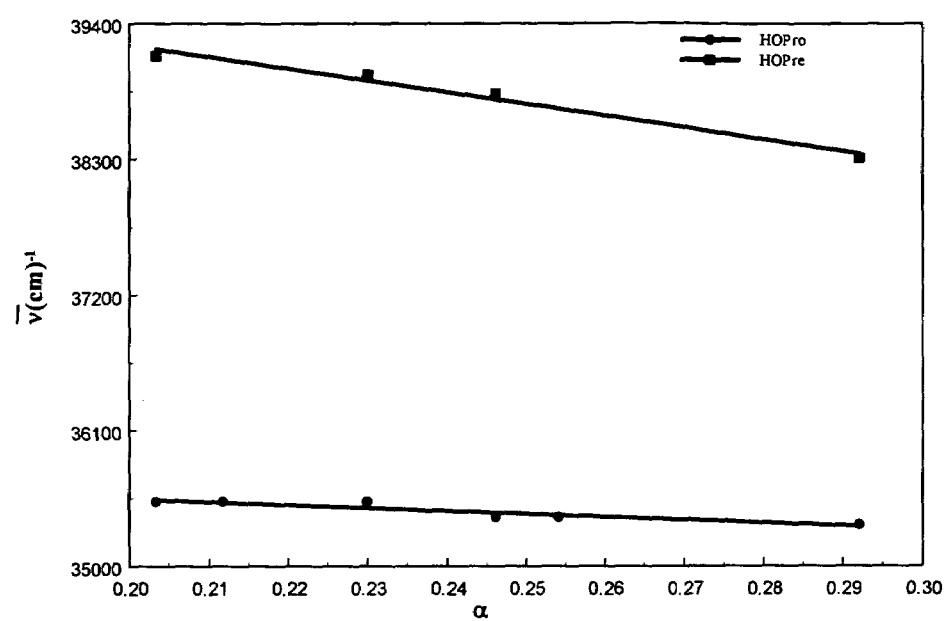
FIG. 7 indicates the dependence of the $I_{max}$ values of the UV spectra of HOPro and HOPre on solvent polarizability at 20° C.;[44] the solvents, in order of increasing polarizability are methanol, acetonitrile, isopropyl alcohol, tetrahydrofuran, dioxane, and toluene.

Irradiation of $Pre_3$ gives a red-shifted relatively structureless spectrum assigned to the cEc conformer of tachysterol because on warming the mixture to 100–105 K in the dark, the spectrum slowly shifts to the blue and develops the well defined vibronic progression of the equilibrium conformer mixture of tachysterol (mainly the tEc conformer), FIG. 5.[28] The initial interpretation that cEc-Tachy was formed from excited cZc-Pre[28a,b] was brought into question because irradiation of the provitamin under nearly identical conditions gives a red-shifted previtamin spectrum, presumed to be the cZc conformer, which on further irradiation gives the structured tEc-Tachy spectrum.[30] The low temperature spectra of Pre[20] and of Pre formed photochemically from Pro are shown in FIG. 6.[27] It was reasoned that the rigid medium prevents the nascent Pre from relaxing to an equilibrium conformer distribution and ensures that its initial geometry is retained, hence accounting for the red-shift in the spectrum. Assignment of the red-shifted spectrum to the cZc conformer of Pre follows from least motion considerations in the highly viscous medium.[27,30] The conformer specific photoisomerization outcomes in Scheme 7 are based on these spectroscopic structural assignments. No experimental mixture spectra have been published and no clear description of the method used to derive the pure component spectrum of the matrix-trapped cZc-Pre conformer shown in FIG. 6 was provided. In accepting such assignments it is important to establish that the transient arises from a one-photon process and that over-irradiation was avoided. These precautions are essential because a sequence of slow light induced s-trans to s-cis conformer equilibration followed by photochemical ring-closure to the cyclobutene has been reported for Ar-matrix isolated 2,3-dimethyl-1,3-butadiene at 19.5 K.[30] Conformer interconversion under these conditions was first reported for 1,3-butadiene[31] and Kohler et al. have shown that excitation of all-s-trans trans,trans-1,3,5,7-octatetraene in an n-octane matrix at 4.2 K leads to s-trans to s-cis conformer conversion[32] and that prolonged irradiation leads to formation of cis,trans-1,3,5,7-octatetraene even at this low temperature.[33] Whether the structural assignments to the Tachy spectra are correct or not, there is no question that these low temperature experiments establish that the absorption spectra of different Tachy conformers differ significantly. This is in agreement with the interpretation of the room temperature Tachy spectrum.

Figure 8:
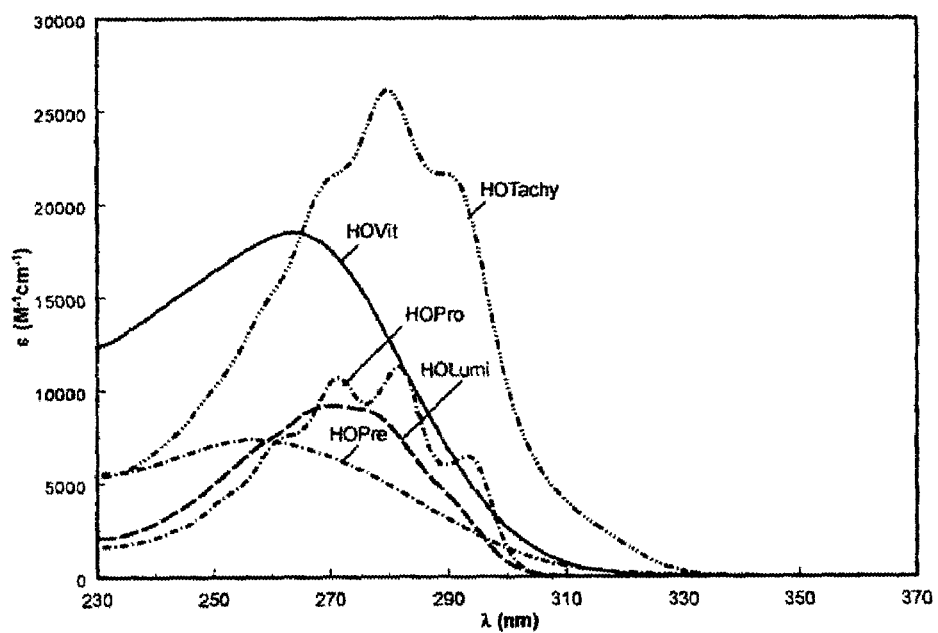
FIG. 8 illustrates UV spectra of HOVit isomers in methanol at 20° C.[44]
Figure 9:
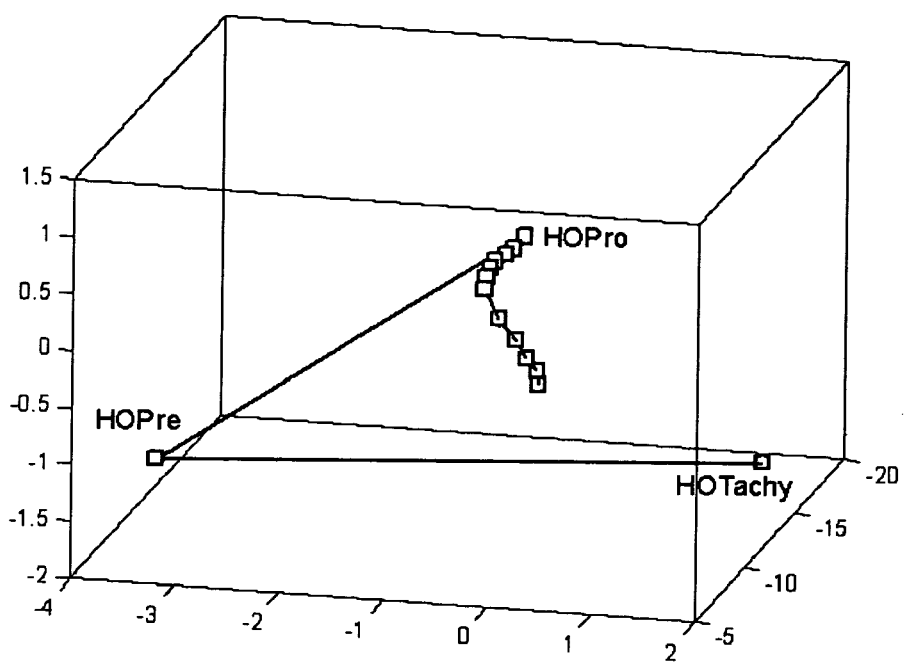
FIG. 9 shows a stoichiometric plane (shown by the labeled pure component points) in SVD combination coefficient space for the 254 nm-irradiation of HOPro in tetrahydrofuran (see text)
Figure 10:
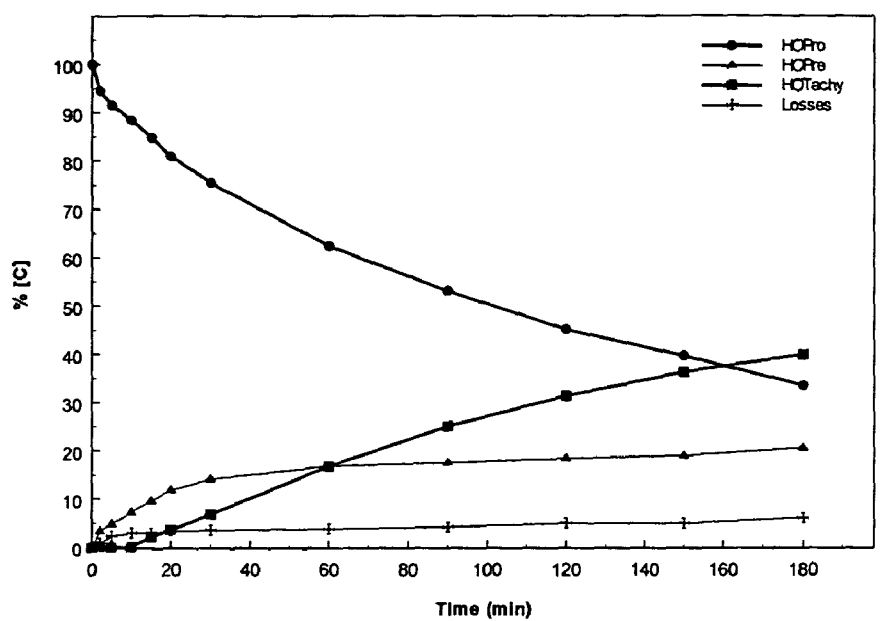
FIG. 10 is a product evolution according to FIG. 9, wherein deviations from the stoichiometric plane are shown as losses.
Figure 11:
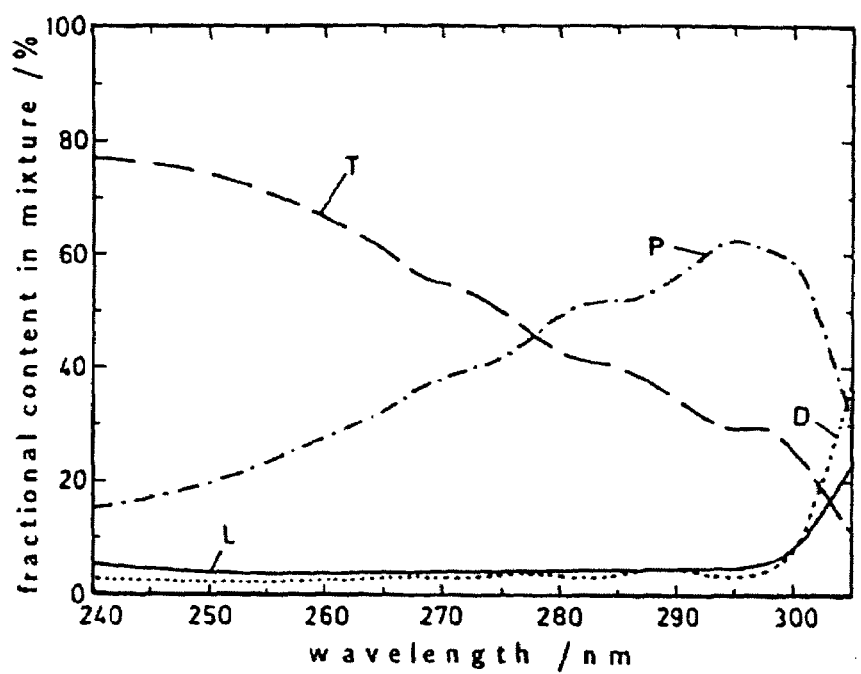
FIG. 11 shows calculated Q-PSS compositions for the $Vit_3$ isomers in ether as a function of excitation wavelength; T, P, L, and D are $Tachy_3$, $Pre_3$, $Lumi_3$ and $Pro_3$ (7-dehydrocholesterol), respectively[24]
Figure 12:
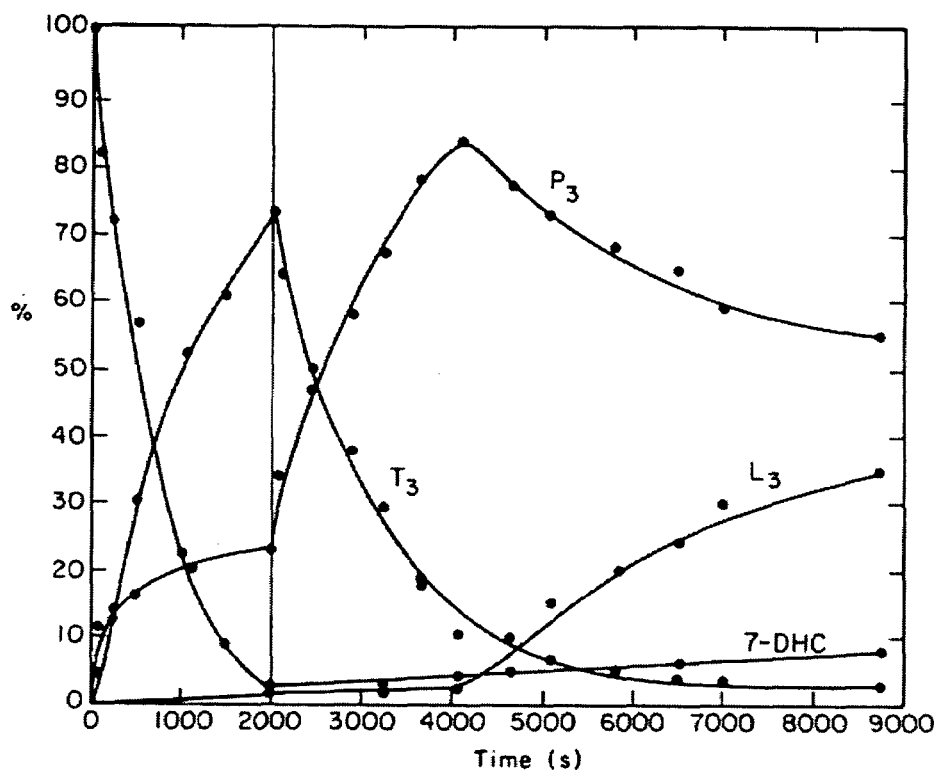
FIG. 12 shows product evolution from the irradiation of $Pro_3$ (7-DHC) in diethyl ether at 0° C. at 254 and then (vertical line at 2000 min) at 350 nm[49]
Figure 13:
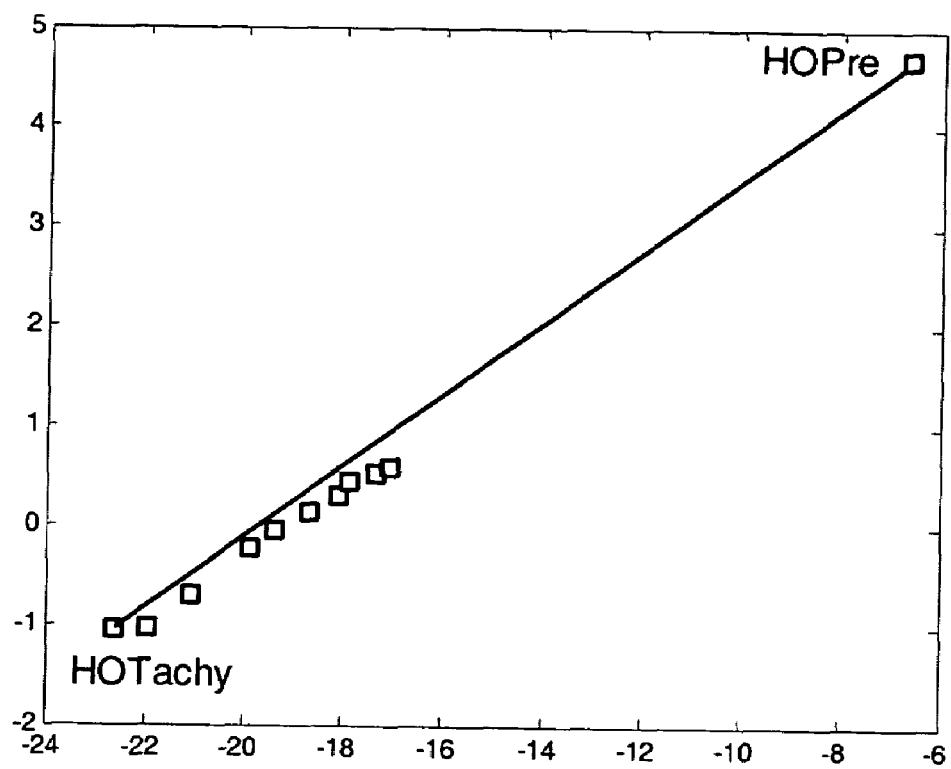
FIG. 13 shows a stoichiometric line in SVD combination coefficient space for the 254 nm-conversion of HOTachy to HOPre in methanol.
Figure 14:
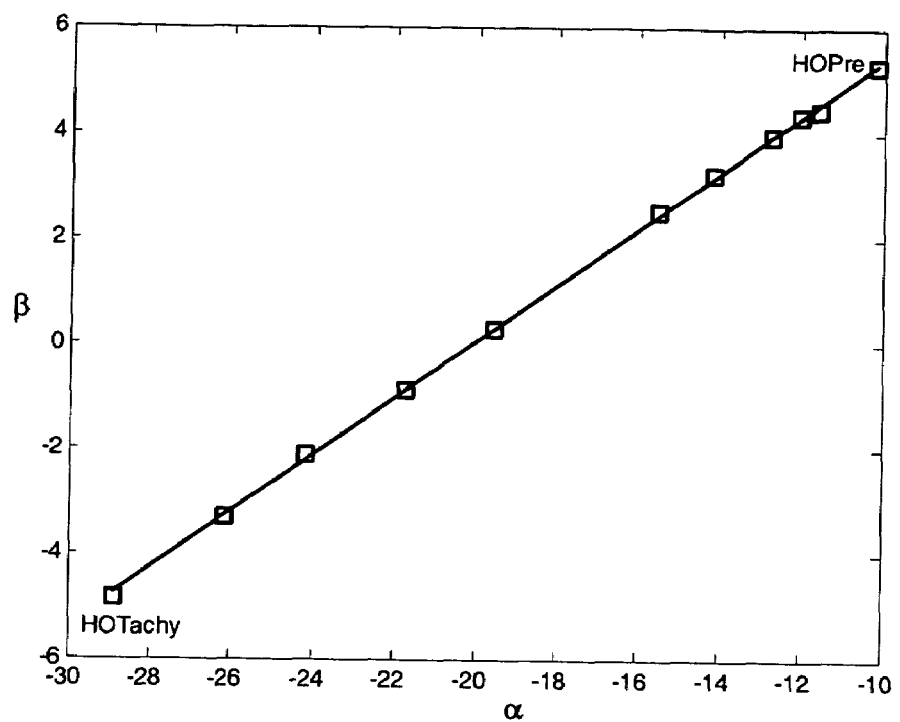
FIG. 14 shows stoichiometric line in SVD combination coefficient space for the 313 nm-conversion of HOTachy to HOPre in methanol.
Figure 15:
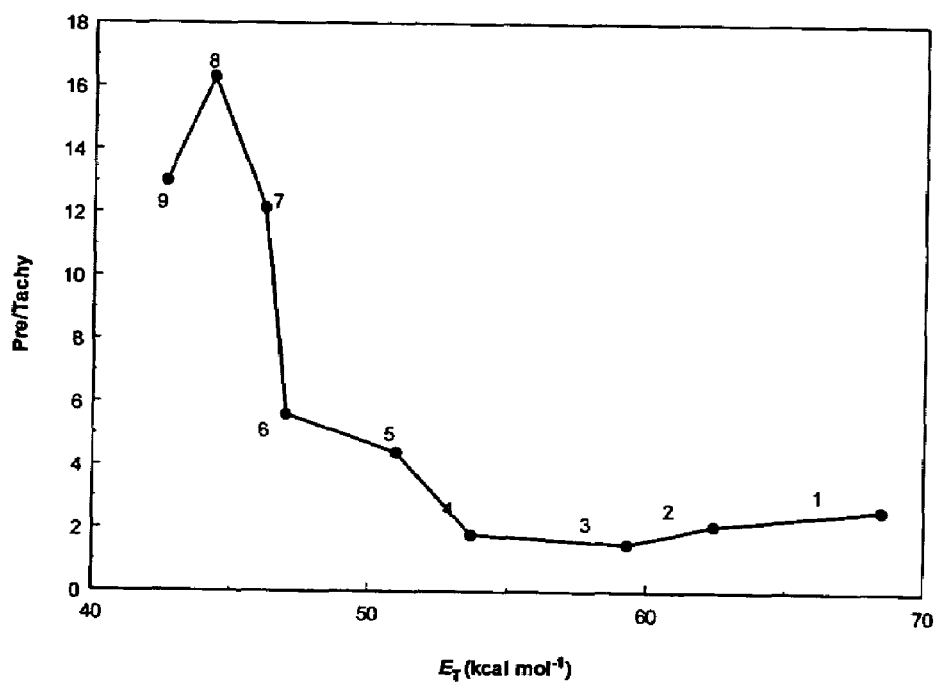
FIG. 15 is a Saltiel plot for the sensitized Pre/Tachy interconversion. Photostationary Pre/Tachy ratios are given for benzophenone (1), anthraquinone (2), 2-naphthyl phenyl ketone (3), benzil (4), fluorenone (5), and benzanthrone (6) for the vitamin $D_2$ system,[61] 2-(6-hydroxy-3-oxo-3H-thioxanthene-9-yl)benzene-sulphonic acid (7) and 7,12-dimethylbenzanthracene (8), for the vitamin $D_3$ system,[64] and anthracene (9) for both vitamin $D_2$ and $D_3$ systems;[62]
Figure 16:
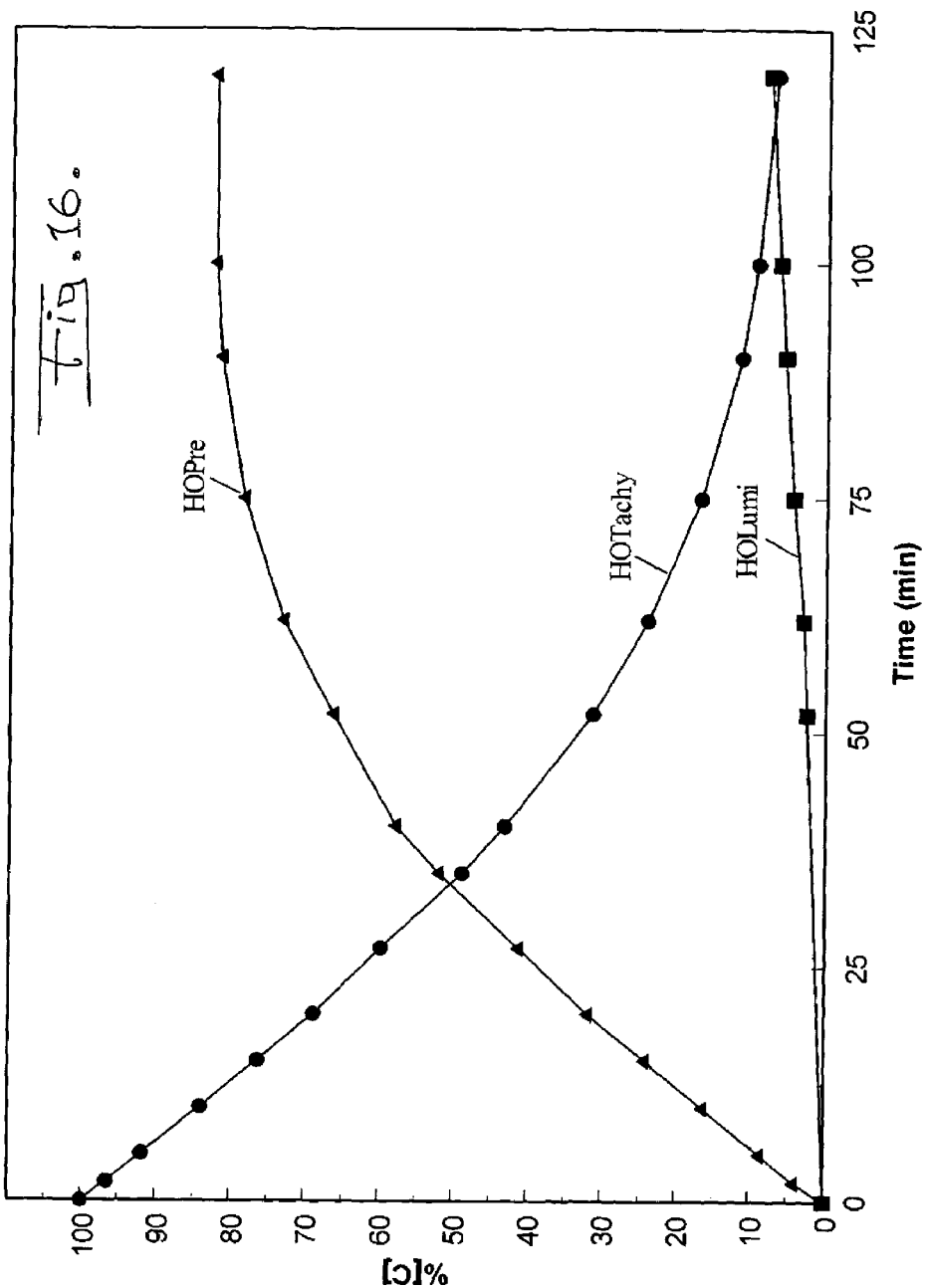
FIG. 16 is a line graph showing the irradiation of HOTachy at 313 nm by SVD analysis.
Figure 21:
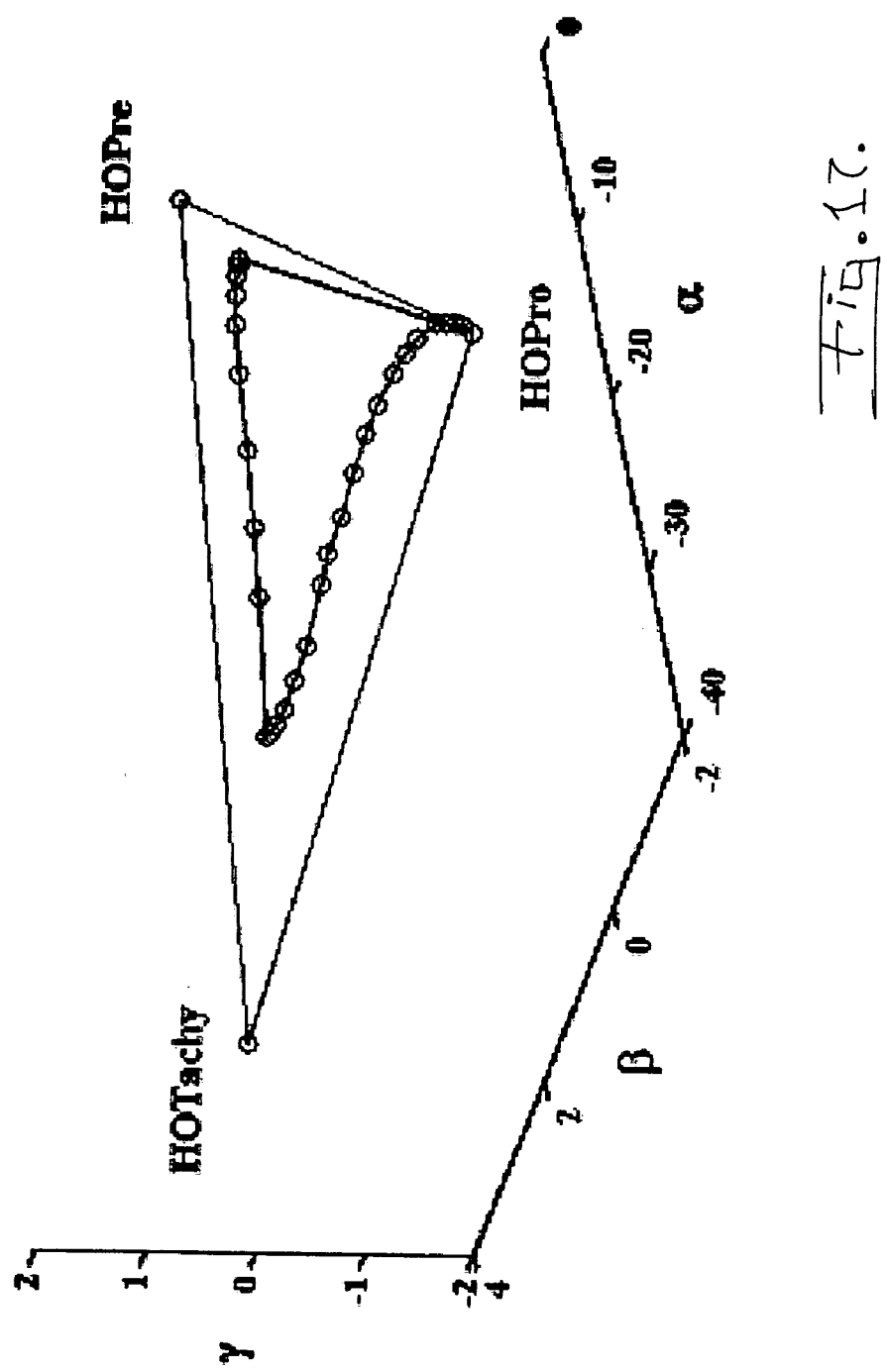

Degassed methanol solutions were employed and conversions were determined by SVD analysis of UV spectra and by HPLC. The quantum yield for the HOTachy⇒HOPre direction in methanol at 20° C. is 0.43, considerably larger than the 0.10 value at 254 nm[1a] (the 0.49 value for the Lumi⇒Pre quantum yield in ether at 313 nm[21] was assigned inadvertently to the Tachy⇒Pre process[47]).[48] The value for this quantum yield in methanol at 254 nm is 0.14. The substantial $\lambda_{exc}$ effect on the quantum yield for the Tachy⇒Pre process indicates that the two wavelengths excite different compositions of HOTachy conformers. SVD analyses of UV spectra of product mixtures obtained in the course of the irradiations of HOTachy in methanol indicate larger losses to products that are transparent at $\lambda_{exc}$<250 nm for excitation at 254 than for excitation at 313 nm. Both spectral matrices behave as two-component systems. However, the combination coefficients for the 254 nm spectral matrix deviate from the HOTachy/HOPre stoichiometric line, FIG. 12, whereas no such deviation is observed for the 313 nm spectral matrix, FIG. 13, at up to 95% conversion to HOPre. Normalizing the spectra of the 254 nm matrix to unit area and performing principal component analysis[10] yields combination coefficients that adhere strictly to the two-component normalization line, consistent with formation of a transparent product as the source of the losses in the SVD analysis.[48] Discussions of the conformational equilibrium in Tachy have settled on the tEc and the tEt conformers as the most energetically favored, with the former being more abundant.[1a,57] The weak structureless band at the onset of the UV spectrum of HOTachy, FIG. 8, would then be assigned to the tEt conformer. An attractive explanation for the wavelength effect is that 254 nm favors tEc-HOTachy excitation, promoting competing trans⇒cis photoisomerization and vinylcyclobutene[1a,58] formation, whereas 313 nm excitation favors excitation of tEt-Tachy whose primary reaction is efficient trans⇒cis photoisomerization, Scheme 8. It appears, therefore, that the 254, 313 nm two-step sequence has advantages over the earlier sequences that employed longer wavelengths in the second step.[55,56] It achieves high, relatively clean Tachy to Pre conversion without requiring long irradiation times due to low absorbance in the second irradiation step and avoids competing Pre photocyclizations to Pro and Lumi.

Scheme 8. Proposed conformer specific photochemistry of HOTachy

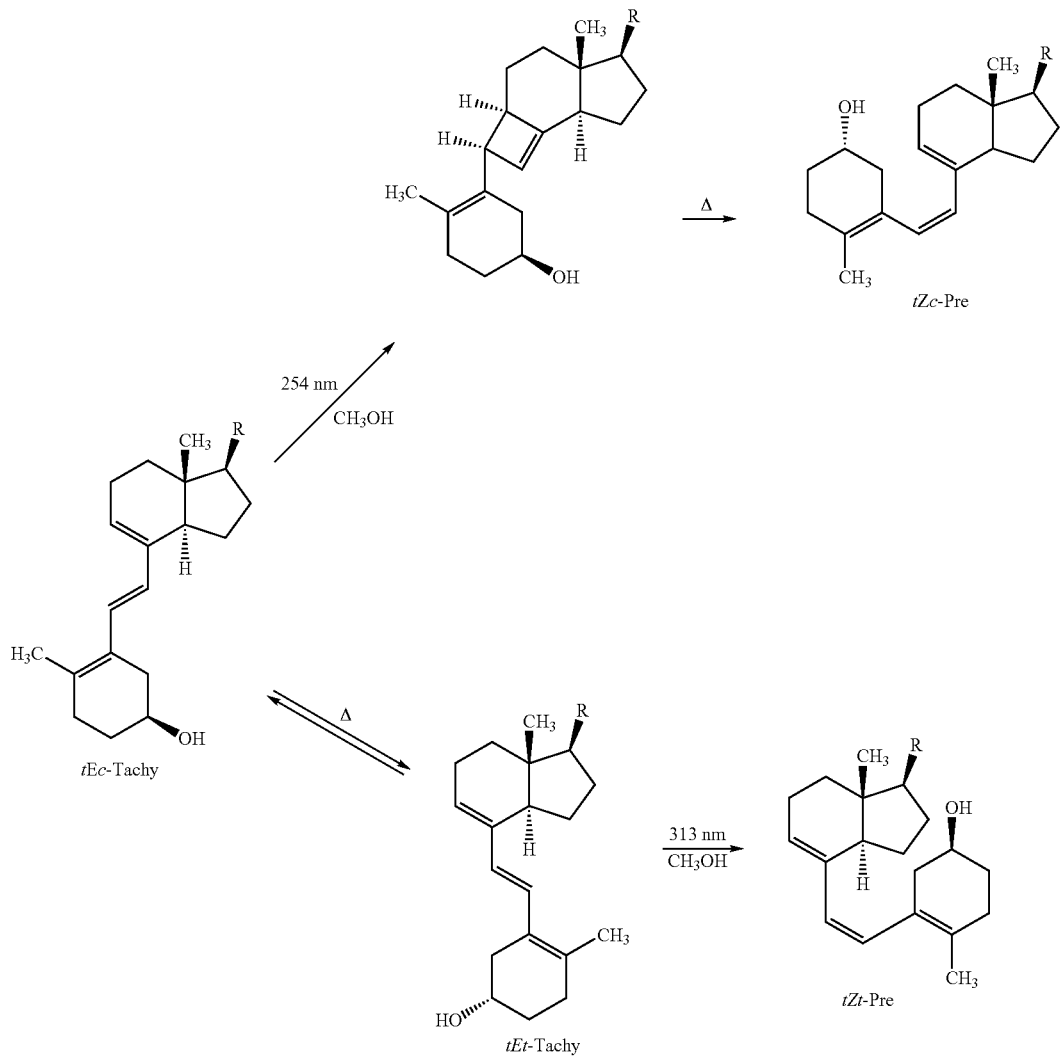

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A process for the production of previtamin D, the process comprising:
    a first irradiation of a reaction mixture containing provitamin D with light energy having a wavelength of approximately 254 nm; and
    a second irradiation of said reaction mixture with light energy having a wavelength of approximately 313 nm, the reaction mixture containing no photosensitizer.

2. The process of claim 1, wherein the first and second irradiations are sequential.

3. The process of claim 1, wherein the reaction mixture further contains a solvent.

4. The process of claim 1, wherein the reaction mixture further contains an organic solvent.

5. The process of claim 1, wherein the reaction mixture further contains methanol.

6. A process for producing previtamin D, the process comprising:
    a first irradiation of a reaction mixture containing provitamin D in the absence of a photosensitizer with light energy having a wavelength of approximately from 240 to 265 nm and a second irradiation of said reaction mixture with light energy having a wavelength of approximately from 300 to less than 330 nm and in the absence of a photosensitizer.

7. The process of claim 6, wherein the first and second irradiations are sequential.

8. The process of claim 6, wherein the reaction mixture further contains a solvent.

9. The process of claim 6, wherein the reaction mixture further contains an organic solvent.

10. The process of claim 6, wherein the reaction mixture further contains methanol.

11. A process for production of vitamin D by light irradiation without the use of a photosensitizer, the process comprising:
- a first irradiation of a reaction mixture containing provitamin D without a photosensitizer with light energy having a wavelength of approximately from 240 to 265 nm;
- a second irradiation of said reaction mixture without a photosensitizer with light energy having a wavelength of approximately from 300 to less than 330 nm; and
- heating the reaction mixture after the second irradiation.

12. The process of claim 11, wherein heating consists of a temperature not exceeding 100° C.

13. The process of claim 11, wherein the first and second irradiations are sequential.

14. The process of claim 11, wherein the reaction mixture further contains a solvent.

15. The process of claim 11, wherein the reaction mixture further contains an organic solvent.

16. The process of claim 11, wherein the reaction mixture further contains methanol.

* * * * *